United States Patent [19]

Yano et al.

[11] 4,409,980

[45] Oct. 18, 1983

[54] GAS SENSOR WITH PH-SENSITIVE FET TRANSDUCER

[75] Inventors: Makoto Yano; Kiyoo Shimada; Kyoichiro Shibatani, all of Kurashiki, Japan

[73] Assignee: Kuraray Company, Limited, Kurashiki, Japan

[21] Appl. No.: 293,304

[22] Filed: Aug. 17, 1981

[30] Foreign Application Priority Data

Aug. 25, 1980 [JP] Japan ................. 55-117411

[51] Int. Cl.³ ............................................ A61B 5/00
[52] U.S. Cl. ................... 128/635; 204/406; 357/25
[58] Field of Search ............ 128/635; 204/195; 324/29; 357/25; 128/630, 631, 632, 633, 634

[56] References Cited

U.S. PATENT DOCUMENTS 3,957,613 5/1976 Macur ........................... 128/635
4,218,298 8/1980 Shimada et al. ............. 128/635

Primary Examiner—Richard J. Apley
Assistant Examiner—T. J. Wallen
Attorney, Agent, or Firm—Oblon, Fisher, Spivak, McClelland & Maier

[57] ABSTRACT

A gas sensor which includes a reference electrode deposited on the surface of a pH-sensitive transducer having a gate-insulated field-effect transistor (FET) structure and adjacent a gate region of the FET, the transducer and reference electrode being housed in a flexible tube so that the gate region of the FET is located in an opening provided at the front end of or on the side wall of the tube. Lead wires connected to the FET and to the reference electrode extend along the tube. Between the inner wall of the tube and lead-wire FET bonding part is placed electrical insulation resin filling to stop the tube. A hydrophilic polymer layer containing electrolyte is provided which at least extends over both the FET gate region and a part of the reference electrode. A gas permeable membrane is laid over the polymer layer.

18 Claims, 13 Drawing Figures

GAS SENSOR WITH PH-SENSITIVE FET TRANSDUCER

BACKGROUND OF THE INVENTION

1. Field of the Invention

The present invention relates to a gas sensor with a pH-sensitive FET transducer (hereinafter referred to as FET transducer) having a gate-insulated field-effect transistor structure.

2. Description of the Prior Art

Measurement of gas concentration such as carbon dioxide or ammonia is of importance in industrial application. Recently, in the medical and physiological fields, importance has been attached to measurement of gas concentration in a living body. For example, it is recognized that measurement of intracellular $CO_2$ gas concentration provides information which is significant from a physiological view-point. In the medical field, continued measurement of monitoring blood $CO_2$ concentration serves the purpose of the state of a patient who is anesthetized, is seriously ill or who is convalescing or provides an indication that a person is in a state of emergency. An extremely small $CO_2$ sensor which is insertible into a cell or blood vessel is needed for the purpose of such a measurement.

A carbon dioxide sensor which has been employed for in the past for such purposes utilizes a miniaturized pH sensitive glass electrode which is shown schematically in FIG. 1. Known as Severinghaus-type $CO_2$ sensor, this sensor consists of a pH-sensitive glass electrode 1, an Ag-AgCl reference electrode 2, an aqueous solution of sodium bicarbonate 3, and a gas permeable membrane 4. The sensor takes advantage of the fact that water-dissolved carbon dioxide dissociates into $H^+$ and $HCO_3^-$ ions.

When it is dissolved in water, a part of the $CO_2$ is transformed into carbonic acid, the dissociation of which results in the formation of protons.

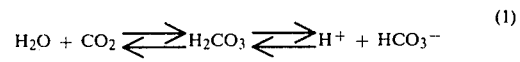  (1)

Therefore, the following relation holds between $CO_2$ concentration in the solution and proton concentration:

$$\frac{[HCO_3^-][H^+]}{[CO_2]} = K \qquad (2)$$

Moreover, $CO_2$ concentration in the solution is proportional to partial gas-phase $CO_2$ pressure $P_{CO_2}$ as follows:

$$[CO_2] = \alpha P_{CO_2} \qquad (3)$$

Use of these formulas, with $-\log[H^+] = pH$ and $\log K = pK$, leads to the relation known as the Henderson-Hasselbalch formula:

$$\log(P_{CO_2}) = -pH + \log[HCO_3^-] + pK - \log\alpha \qquad (4)$$

Here, if the aqueous solution contains no electrolyte that will produce bicarbonate ion, such as $NaHCO_3$, or proton source other than $CO_2$, the relation $[H^+] = [HCO_3^-]$ holds. Accordingly, $$\log(P_{CO_2}) = -2pH + pK - \log\alpha \qquad (5)$$

Under a constant temperature condition, both K and $\alpha$ are constant. Thus, formula (5) may be rewritten:

$$pH = -\tfrac{1}{2}\log(P_{CO_2}) + \text{constant} \qquad (6)$$

Where, in the solution, $NaHCO_3$ is present excessively relative to $CO_2$, $[HCO_3^-]$ is also constant. Then, from formula (4) is derived the following relation:

$$\text{the } pH = -\log(P_{CO_2}) + \text{constant} \qquad (7)$$

As is apparent from the above discussion, pH of the solution varies in proportion to the logarithm of partial $CO_2$ pressure. In the light of this fact, the amount of $CO_2$ in solution can be determined by means of a pH-sensitive electrode. In this connection, it is noted that, as can be seen from a comparison between formula (6) and formula (7), electrolytes such as $NaHCO_3$ present in solution serve to double the proportional coefficient in proportional relation between pH and $\log(P_{CO_2})$, that is, the output of the pH-sensitive electrode.

There are various kinds of gases, including $CO_2$, that will dissolve in water to form proton ions and change the pH of the aqueous solution, as listed below.

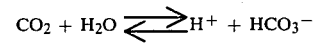

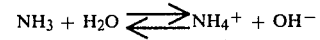

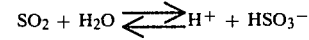

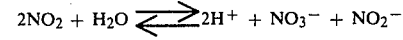

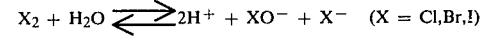

Quantitative analysis by means of a pH sensitive electrode can be made also with acids which are not of such type as will dissolve in water to form hydrogen ion but which have more than a certain degree of vapor pressure. For example, acetic acid gas will dissolve in water to form hydrogen ion.

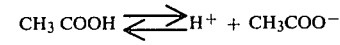

In the light of such reaction, an ammonia-gas sensor can be constructed which consists essentially of a gas permeable membrane, an aqueous phase including ammonium-ion containing salt or polyions, an Ag-AgCl electrode and a pH-sensitive electrode.

A sulfur-dioxide sensor may utilize an aqueous phase including sulfite-ion containing salt or polyions.

Various types of gas sensors based on the above discussed principle, where used in the medical and physiological fields and more particularly in measuring gas concentration in a living body, are employed in such a way that the sensor is inserted into a tissue of the living body. To this end, it is necessary that such a gas sensor should be microminiaturized. In other words, miniaturized pH-sensitive electrodes are needed. However, it has been recognized that miniaturization of conventional-type glass electrodes involves the following problems:

(a) The resistance of the glass membrane is limited to about 10 MΩ. Therefore, an amplifier with a higher input resistance is required.

(b) The membrane is so thin that its mechanical strength is low.

(c) Decreased electrode area will result in higher membrane resistance.

All this means that a larger and more complicated measuring apparatus is required. Moreover, the glass electrode is fragile and more liable to breakage. From the view point of practical application, these are problems with a gas sensor using a glass electrode which is designed to be inserted into a tissue of a living body for measurement of gas concentration in the body.

A $CO_2$ sensor using a solid pH electrode of metallic oxide in place of a glass electrode is disclosed in U.S. Pat. No. 3,719,576. This electrode, smaller and more slender than a sensor using a glass electroe, is more suitable for use as such for insertion into the tissue of a living body, but it involves these difficulties:

(a) The sensor is non-flexible because of the solid electrode.

(b) Higher electric resistance due to smallness in size.

These difficulties can be eliminated by using a recently developed pH-sensitive FET transducer having a gate-insulated field-effect transistor structure instead of a glass electrode or solid electrode. A gas sensor incorporating such pH-sensitive FET transducer, as disclosed in Japanese laid-open patent application No. 53-149396, is of such construction that a pH-sensitive FET transducer and a reference electrode are housed in a tube, in spaced apart relation, and electrical insulation resin is deposited between lead-wire FET joints and the wall of the tube to stop the tube, a gas-permeable membrane being laid at the front end of the tube, with electrolyte placed in the space formed between the tube wall and the membrane. However, there are constructional difficulties with said gas sensor using the FET transducer, as follows:

(a) Miniaturization of a gas sensor requires a smaller electrolyte chamber, which means less amount of electrolyte deposited in the chamber. This makes it difficult to perform prolonged continuous measurement, if electrolyte leaks and evaporation during measuring operation are considered.

(b) The fact that the reference electrode and FET transducer are housed in the tube in spaced apart relation limits the possibility of miniaturization.

(c) The spaced-apart relation between the reference electrode and the FET transducer gives rise to greater electric resistance between the reference electrode and the FET transducer gate, with the result that noise from such sources as induction current is likely to be introduced.

A $CO_2$ sensor designed to overcome such difficulties with the known gas sensor using the pH-sensitive transducer was proposed by T. Matsuo et al. at the 18th convention of the Japanese ME Society (May 1979). This sensor, as FIG. 2 shows, is of such construction that a pH-sensitive FET transducer 5 having a Ag-AgCl reference electrode 6 deposited thereon is placed in a glass tube 7, and electric insulation resin filling 8 is present between lead-wire-FET joints and the inner wall of the tube to stop the tube, with an aqueous solution of sodium bicarbonate placed in a space 9 defined between a gas-permeable membrane 10 and the Ag-AgCl and FET gate. However, this sensor has the disadvantage that the Ag-AgCl layer deposited on the $Si_3N_4$ surface of the FET transducer is liable to separate from the $Si_3N_4$ surface during measuring operation, because silver does not exhibit good adhesion with $Si_3N_4$. This sensor is made in the following way. An Ag-AgCl reference electrode 6 is deposited on the surface of a FET transducer 5. Thereafter an aluminum layer is deposited which extends over both the gate region of the FET transducer and a part of the reference electrode. A fluoroplastic coat is placed on the surface of the aluminum layer to provide a gas-permeable membrane. Then, the aluminum layer is removed by electrolysis so that a space is formed between the fluoroplastic layer and the FET transducer gate and a portion of the reference electrode. Electrolyte is injected by means of a syringe into the space. The injection hole is stopped with slicone resin. One difficulty with this process is that the silver in the reference electrode is contaminated with aluminum as a result of the method used for forming the space. This leads to unstable signalling. Moreover, the complexity involved in the manufacturing process makes it very difficult to manufacture a reasonably reproducible sensor.

After extensive research directed for eliminating the difficulties with the $CO_2$ sensor proposed by T. Matsuo et al., the inventors developed an improved gas sensor of novel construction.

SUMMARY OF THE INVENTION

One of the objects of the present invention is to provide a gas sensor which can constantly give stable and correct measurements over a long period.

It is another object of the invention to provide a microminiature gas sensor which is insertible into a living body.

It is a further object of the invention to provide a gas sensor which can be easily manufactured and adapted for volume production.

The gas sensor of the invention comprises a reference electrode deposited on the surface of a pH-sensitive transducer having a gate-insulated field-effect transistor (FET) structure and adjacent a gate region of the FET, the transducer and reference electrode being housed in a flexible tube so that the gate region of the FET is located in an opening provided at the front end of or on the side wall of the tube, lead wires connected to the FET and to the reference electrode and which extend along the tube, electrical insulation resin filling the space between the inner wall of the tube and lead-wire-FET joints to stop the opening of the tube, an electrolyte-containing hydrophilic polymer layer stretching at least over both the FET gate region and a part of the reference electrode, and a gas permeable membrane placed over the polymer layer.

DETAILED DESCRIPTION OF THE PREFERRED EMBODIMENTS

Figure 1:
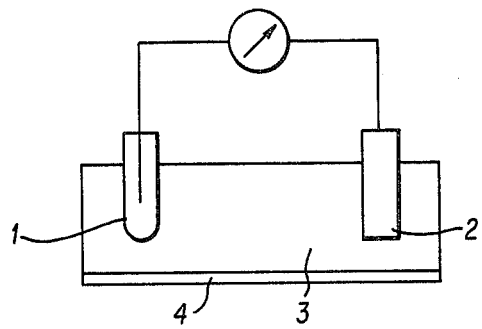
FIG. 1 is a schematic view illustrating the principle of measuring operation of a $CO_2$ sensor using a glass electrode.
Figure 2:
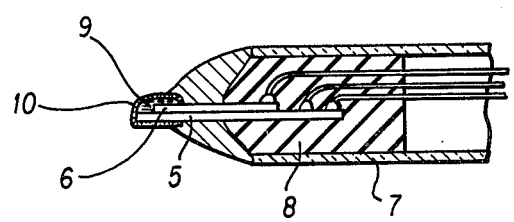
FIG. 2 is a fragmentary sectional view of a conventional $CO_2$ sensor with a pH-sensitive FET transducer.
Figure 3:
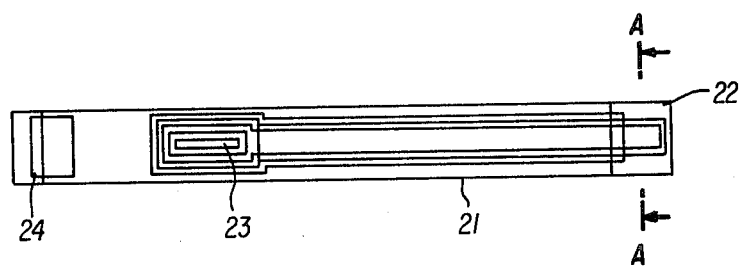
FIG. 3 is a plane view showing a pH-sensitive FET transducer employed in the gas sensor of the present invention.
Figure 4:
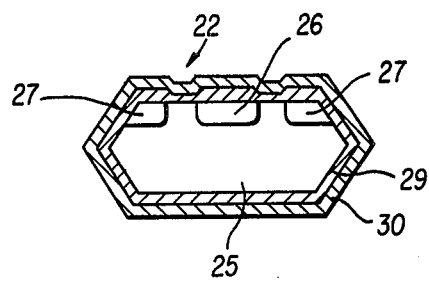
FIG. 4 is a section taken on line A—A in FIG. 3.

Referring to the drawings, FIG. 3 is a plane view showing a pH-sensitive FET transducer 21 employed in the gas sensor of the present invention. The FET transducer 21 has an elongated configuration, for example, 0.4 mm wide and 3-4 mm long, and is provided with a gate region 22 at one end and a drain terminal 23 and a source terminal 24 at the other end or adjacent thereto. For detailed construction of such FET transducer, reference is made to U.S. Pat. No. 4,218,298 which discloses a selective chemical sensitive FET transducer proposed by the inventors. As can be seen from FIG. 4 which shows a section taken on line A—A in FIG. 3, the gate region 22 has a drain diffusion region 26 and a source diffusion region 27, both formed on a silicon substrate 25, the entirety of the gate region 22 being covered with two layers, that is, an oxidized layer 29 and a surface stabilizing layer 30 laid thereon. Surface stabilizing layer 30 may be of silicon nitride ($Si_3N_4$), alumina ($Al_2O_3$) or tantalum pentoxide ($Ta_2O_5$). A sensor having such a layer is sensitive to hydrogen ion. Actually, a silicon nitride layer of 1,000Å or so, when used as a surface stabilizing layer, provides a surface potential of 53-56 mV/pH, substantially same as one obtainable with conventional glass electrode, in the pH range 1-13.

Figure 5:
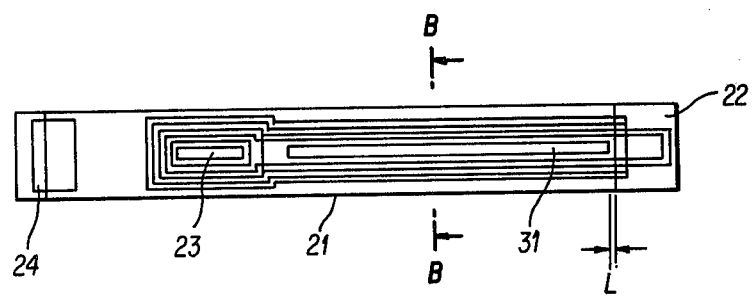
FIG. 5 is a top plan view showing a reference electrode deposited on the surface of the FET transducer in FIG. 3.
Figure 6:
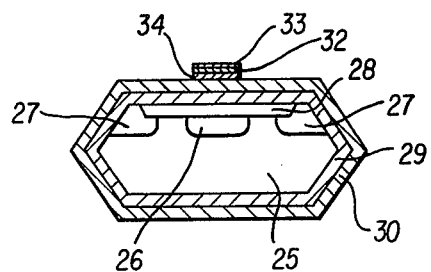
FIG. 6 is a section taken on line B—B in FIG. 5.

FIG. 5 is a plane view showing a reference electrode 31 deposited on the substrate of FET transducer 21 in close relation to the gate region of the FET. As shown in FIG. 6 which is a section taken on line B—B in FIG. 5, the reference electrode 31 is formed of silver (Ag) 32 and silver chloride (AgCl) 33, for example. Such Ag-AgCl layer may be formed by vacuum evaporation, electrolytic metal plating and electrolytic chlorination. Usually with known FET gas sensors, an Ag-AgCl layer is deposited on a FET substrate without provision of a bonding layer between. Generally, however, silver does not form a good bond with surface stabilizing layer 30 in the FET transducer. Therefore, it is desirable to provide, because the silver layer and the surface stabilizing layer, a bonding layer 34 which will form a good bond with both of said layers. If the surface stabilizing layer is of silicon nitride, such materials as chromium, chrome copper and nickel may be suitable for use as bonding layer 34. Shown at 28 is a channel stopper layer. The thickness of the bonding layer 34 and Ag-AgCl layers, 32, 33 on the silicon nitride layer 30 has great bearing upon both stability and serviceability of the sensor. Therefore, the thickness of the bonding layer 34 provided on the silicon nitride layer 30 is preferably 100-1,000Å. If the thickness of the bonding layer is not more than 100Å, the bonding layer will not provide any sufficient bond. A thickness greater than 1,000Å provides no advantage worthy of the length of time required in depositing the bonding layer; rather, it will make the layer liable to separate. Silver layer 32 and silver chloride layer 33 on the bonding layer should not be made too thin. Unreasonably thin silver and silver chloride layers will be a cause of unstable measurement or severe drift and will render the sensor unserviceable, though the sensor may work properly just after manufacture thereof. Therefore, to ensure good serviceability of the sensor, the thickness of the silver layer is preferably more than $3\mu$ and that of silver chloride layer is preferably more than $1\mu$. Formation of a Ag-AgCl layer may be performed, for example, by thinly depositing a chrome layer over the $Si_3N_4$ layer on the FET, placing thereon a silver layer by vacuum evaporation or electrolytic metal plating, then subjecting the layers to electrolysis in a NaCl solution, with the deposited Ag as anode, so that the silver layer surface is chlorinated. Thus, an Ag-AgCl reference electrode is formed. In order to provide a relatively thick silver layer, it is desirable that a thin silver layer be formed by vacuum evaporation, then a sufficiently thick silver layer be formed thereon by electrolytic metal plating. The configuration and disposition of the reference electrode are also important. If the distance L between the gate region and the reference electrode (FIG. 5) is relatively large, the sensor is liable to exhibit noise due to induction. Therefore, the distance L between the gate region and the reference electrode is preferably less than 2 mm. Where the distance is less than 2 mm, there is no noise problem from a practical point of view. In order to prevent short circuiting between the reference electrode lead wire joints and the FET gate region, it is desirable that the reference electrode should have an elongated configuration similar to that of the FET transducer, with lead wires connected to one of its ends and the lead joints spaced as much apart from the gate region as possible.

Figure 7:
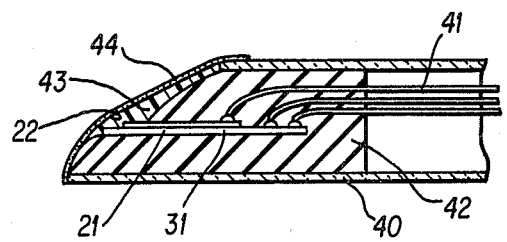
FIG. 7 is a fragmentary sectional view of the gas sensor of the invention.
Figure 8:
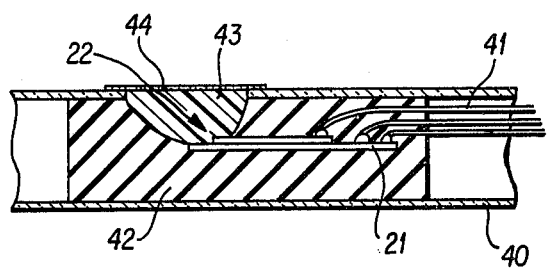
FIG. 8 is a sectional view showing another form of gas sensor according to the invention.

FIG. 7 is a fragmentary sectional view showing the construction of the gas sensor of the invention. The pH-sensitive FET transducer 21 has a substrate on which is deposited the reference electrode 31 shown in FIGS. 5 and 6. The transducer 21 is housed in a flexible insulation tube 40 or, for example, the front portion of a catheter, of such material as polyethylene, polypropylene, polytetrafluoroethylene, silicon, nylon 11, polyvinyl chloride, or polyethelene terephthalate, with its gate region 22 exposed in the front opening of the insulation tube 40. Individual lead wires 41 connected to the reference electrode 31 and FET transducer 21 are insulation-coated and passed through the insulation tube, with their ends drawn out of the rear end of the tube. For the purpose of protecting the FET transducer 21 from breakage, the front opening of the insulation tube 40 extends beyond the front end of the tranducer. Further, said front opening is diagonally cut away so that it is easily insertible into a living body. The space between the FET transducer 21, reference electrode 31, lead-wire-FET joints and the inner wall of the insulation tube is packed with electrical-insulation resin 42, such as epoxy resin or silicone resin, whereby the front portion of the insulation tube is stopped. FIG. 8 shows another form of gas sensor according to the invention. A pH-sensitive FET transducer 21, together with a reference electrode 31 deposited on its substrate as shown in FIGS. 5 and 6, is housed in an insulation tube 40, with its gate region exposed in an opening provided on a side portion of the tube 40. Electrical insulation resin 42 is packed in the tube, except said opening and the space occupied by the FET gate region and a part of the reference electrode, to stop the tube. A hydrophilic polymer layer 43 containing electrolyte which is liable to pH variation through gas absorption is provided in such a way that the layer 43 lies over both the gate region 22 and the reference electrode 31. The thickness of the polymer layer is preferably 1–10μ. If the thickness is more than 10μ, response speed will be reduced, whereas if it is less than 1μ, signalling will be unstable. Therefore, the polymer layer must be reasonably thin and uniform in thickness.

Polymer employed for the purpose of this invention must have a reasonable degree of water pickup (60 weight % or more at 37° C., temperature of measurement) and must be substantially free from organic acid groups such as the COOH group and basic groups, or if present, should be present in an amount of 2 mole % (relative to total monomer unit) or less. Low water pickup will reduce response speed. Any unreasonable organic-acid-group or basic-group content will adversely affect sensitivity. Among suitable polymers as such as polyvinyl alcohol (hereinafter referred to as PVA), cellulose, polyhydroxyethyl methacrylate, polyvinyl pyrrolidone, agar-agar, starch, and electrolyte polymer. These polymers may be copolymerized with monomers or may contain plasticizers or the like. Of these polymers PVA is particularly suitable with respect to stability. The polymerization degree for PVA is preferably 500–30,000.

The polymer chain of PVA, as the following formula indicates, includes, in addition to normal vinyl alcohol unit (B), various carbonyl-containing hetero units such as terminal aldehyde group (A), ketone group (C), vinyl acetate group (D), and terminal carboxyl group (E).

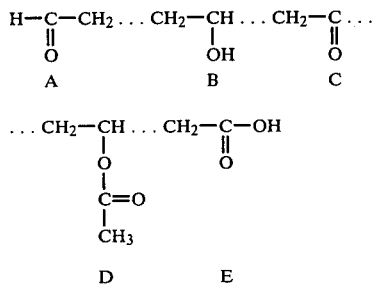

Of these hetero units, terminal aldehyde and ketone groups are transformed into the enol form through keto-enol isomerization; and the enol-form groups act as weak acid groups. Vinyl acetate groups are saponified to form acetic acid. Terminal carboxyl groups in their form as such, act as an acid. So, all these carbonyl-containing hetero units act as acid groups, thus adversely affecting the sensitivity of the gas sensor. For the purpose of gas sensor of the present invention, therefore, it is desirable that such hetero unit content, as a whole, in PVA should be no more than 2 mole % relative to total monomer unit.

PVA may be in the form of copolymer formed through copolymerization with such monomers as vinyl pyrrolidone and vinylene carbonate. Both PVA and vinyl alcohol copolymer, if they are plasticized, are more stable against drying. The following are suitable for use as plasticizers for the purpose of this invention: ethylene glycol, diethylene glycol, trimethylol propane, 3-methyl-1,3,5-pentane triol, butanediol, triethylene glycol, dipropylene glycol, glycerin, and polyvinyl pyrrolidone.

Polymer content (percentage of polymer against polymer plus plasticizer) in the hydrophilic polymer layer 43 is preferably 50 weight % or more but not more than 95 weight % in dry condition. Any smaller polymer content will lead to decreased water pickup and decreased shape-holding ability and accordingly may be a cause of electrical contact break between the gate and the reference electrode during prolonged use or storage. If the polymer content is more than 95 weight %, the sensor will be liable to deterioration in sensitivity and response speed.

The electrolyte content of the polymer layer, if unreasonably low relative to the amount of polymer, will be a cause of decreased sensitivity and signal instability. Unreasonably high electrolyte concentration will be a cause of decreased response speed. Therefore, it is essential that electrolyte content should be moderate enough to cause no such trouble. For example, in the case of $CO_2$ sensor, the $NaHCO_3$ content is preferably 0.01–1 mol and the NaCl content is preferably 0.1–2 mol relative to the polymer content. A polymer layer containing such electrolyte material may be prepared by dissolving polymer and electrolyte in a solvent which can solve both of them, for example, water, coating the solution, then drying the coat. Alternatively, it is desirable to prepare a polymer layer by applying a solution consisting solely of a polymer, or by carrying out polymerization on the gate, subject same to crosslinking, if possible, immerse the layer in an electrolyte solution, cause same to swell, and then dry. In either case, for the purpose of drying, freeze drying is preferable so that swollen-state thickness may be retained.

The hydrophilic polymer layer 43 is covered with a gas-permeable polymer 44.

For the purpose of this polymer 44, a known gas-permeable membrane may be used. Among known membranes as such are fluoroplastics which are polymers and copolymers of polytetrafluoroethylene, trifluoroethylene, hexafluoropropylene, chlorotrifluoroethylene and the like, and polyolefin plastics, silicone resins such as polyethylene, polypropylene, polypentene-1, and the like. Of these, polytetrafluoroethylene and silicon resins are most preferable; use of the former makes it possible to obtain a sensor less liable to change with time, and the latter a sensor with a shorter response time. Membrane thickness is preferably 3–20μ with fluoroplastics and 50–300μ with silicone resin from the view points of strength and response time.

For the purpose of coating the gas permeable membrane, various methods such as dip coating, spray coating, vacuum evaporation, ultraviolet photo-polymerization, plasma polymerization, and sputtering may be used. To ensure satisfactory response speed, the gas permeable membrane must be uniform and thin. More especially, nonrubber-form polymers, such as polytetrafluoroethylene, polyethylene, and polypropylene, must be of thin configuration; and for this purpose, use of a vapor-phase polymerization method, such as vacuum evaporation, ultraviolet photo-polymerization, plasma polymerization, or sputtering, is preferred. It is also possible to have a gas-permeable tube, the front end of which is closed, laid over the gate region of the sensor, with the other end of the tube fixed liquid-tightly to the sensor. This method is particularly preferred for a sensor having an elongated configuration, because it permits miniaturization of such a sensor.

The gas sensor in its as manufactured state will not work, because its hydrophilic polymer layer is in a dry state. The sensor is put in use after the hydrophilic polymer is caused to pick up moisture or swell in water or in vapor. The sensor, once dried, may be effectively reused after prolonged immersion in water. For immediate use, the sensor is preferably stored in water. The sensor of the invention is not susceptible to problems because of prolonged storage in water, such as base line drift, decreased response speed and reduced sensitivity.

The gas sensor of the present invention may be manufactured in the following manner:

(1) Reference electrode 31 is deposited on the surface of pH-sensitive FET transducer 21 (FIG. 3) in manner as shown in FIG. 5.

Figure 9:
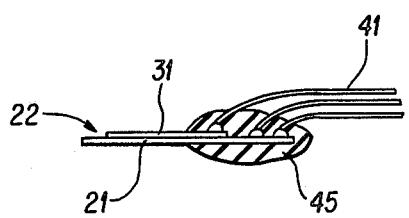
FIGS. 9-11, inclusive, are fragmentary sectional views illustrating the method of manufacturing the gas sensor of the invention.
Figure 10:
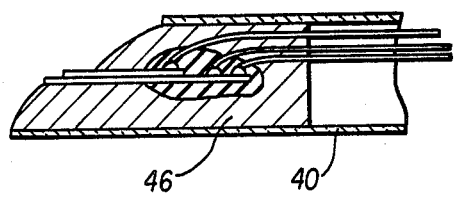

(2) Lead wires 41 are connected to reference electrode 31 and FET transducer 21, and peripheral area is insulated with epoxy resin (FIG. 9). FET transducer 21 is housed in catheter 40, with gate region 22 of transducer 21 disposed in front opening of catheter 40. Thereafter, epoxy resin 46 is filled in between leadwire-FET joints and the inner wall of the catheter to stop the front portion of the catheter. (FIG. 10)

Figure 11:
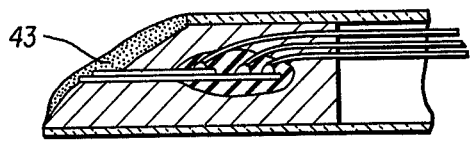

(3) A hydrophilic polymer layer 43 is laid over both gate region and reference electrode (FIG. 11). In this case, polymer layer is so arranged that it mounts over the entire surface of the gate region and a portion of comparison electrode.

(4) Hydrophilic polymer layer 43 in the dry state is covered with gas-permeable membrane 44. (FIG. 7)

A gas sensor so manufactured will not work in its as manufactured state as such. So, it is subjected to moisture pickup and swelling in water or vapor before it is put in use.

Figure 12:
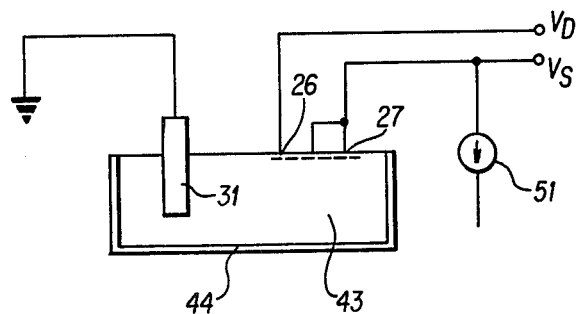
FIG. 12 is an electric circuit diagram incorporating the gas sensor of the invention.
Figure 13:
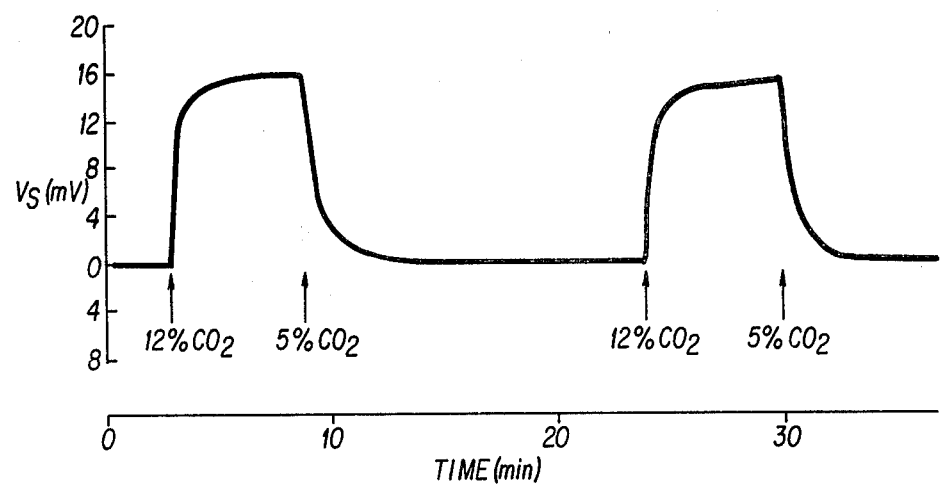
FIG. 13 is a graphical representation showing $CO_2$ response of $CO_2$ gas sensor of the invention.

Measuring operation with the sensor is performed through the circuit shown in FIG. 12.

The circuit shown is a source follower circuit. The reference electrode is grounded. A constant voltage $V_D$ is applied to drain 26. A constant current flows between drain 26 and source 27 via constant current circuit 51. As it passes through gas-permeable membrane 44, gas is absorbed into the electrolyte contained in the hydrophilic polymer layer 43 to change the surface potential of gate region 22 of the FET transducer 21 exposed to the polymer layer. The change in surface potential is followed by a change in source potential $V_s$. Accordingly, by measuring potential between output terminal 52 and reference electrode 31, it is possible to determine hydrogen ion concentration in the polymer layer, that is, gas concentration in the solution.

EXAMPLE 1

On the surface of a pH-sensitive FET transducer were deposited a Cr layer of 0.03μ and a Ag layer of 1μ, in manner as shown in FIGS. 5 and 6. An AgCl layer of 3μ was formed thereon by electrolytical metal plating. The FET transducer so deposited with layers was inserted into a catheter. After depositing of epoxy resin into the space between the inner wall of the catheter and the FET transducer and the reference-electrode leadwire joints, the sensor gate region and a portion of the reference electrode were covered with a 5μ polyvinyl alcohol (porimerization degree: 1700) layer containing 1.5 mol % carbonyl group, which includes 1.0 N NaCl, 0.1 N NaHCO$_3$ and 30% glycerin as a plasticizer, as illustrated in FIG. 11. A silicone tube having a wall thickness of 100μ and sealed at one end thereof was inserted into the catheter through the first end of the gate portion. The tube, at the other end thereof, was bonded liquid-tightly to the catheter with silicone resin. A carbon dioxide sensor was thus prepared.

The sensor was immersed in water, whereby the PVA layer was allowed to swell until its water content reached more than 60%, at 37° C.

Into nitrogen gas currents containing 5% and 12% carbon dioxide at 25° C. was inserted the sensor for measurement. The sensor exhibited remarkable performance, with signal difference 16 mV (theoretical value 22 mV) and 50% response speed 20 sec. The sensor maintained stable output at ordinary room temperature, day and night. When dried, the sensor was made reusable by immersing it in water at 50° C. for 2 hours.

EXAMPLE 2

Carbon dioxide sensors were made in manner as described in the Example 1, except that the composition, formulation, and thickness of hydrophilic polymer layer containing CO$_2$-absorbing electrolyte were varied. Measurements were made with respect to sensitivity (output difference at 12% CO$_2$ and 5% CO$_2$), time required for ½ response when CO$_2$ concentration was changed from 12% to 5%, and performance stability. Results are presented in Table 1.

TABLE 1

| | Type of Polymer | Plasticizer wt %/polymer | NaHCO$_3$ mol/l/ polymer | NaCl mol/l/ polymer | polymer layer thickness in dry state (μ) | Sensitivity (mV) | Response time (sec.) | Stability | Evaluation | Remarks |
|---|---|---|---|---|---|---|---|---|---|---|
| 1 | PVA (carbonyl group cont. 12 mol % or less; polymerization degree 2400) | — | 0.1 | 1 | 5 | 10 | 25 | noisy | X | unstable |
| 2 | PHEMA *1 | — | 0.1 | 1 | 5 | 13 | 60 | 0 | 0 | |
| 3 | Cellulose | Glycerin 30% | 0.1 | 1 | 10 | 14 | 50 | 0 | 0 | |
| 4 | E V A *2 | — | 0.1 | 1 | 5 | — | — | noisy | X | unstable |
| 5 | PVA (carbonyl gr. cont. 0.5 mol % or less; pol. deg. 1700) | Glycerin 30% | 0.1 | 1 | 5 | 15 | 30 | 0 | 0 | |
| 6 | PVA (carbonyl gr. cont. 0.5 mol % or less; pol. deg. 1700) | Ethylene glycol 120% | 0.1 | 1 | 5 | 18 | 30 | noisy | X | unstable |

TABLE 1-continued

| | Type of Polymer | Plasticizer wt %/polymer | NaHCO$_3$ mol/l/ polymer | NaCl mol/l/ polymer | polymer layer thickness in dry state ($\mu$) | Sensitivity (mV) | Response time (sec.) | Stability | Evaluation | Remarks |
|---|---|---|---|---|---|---|---|---|---|---|
| 7 | PVA (carbonyl gr. cont. 0.5 mol % or less; pol. deg. 1700) | Ethylene glycol 30% | 0.1 | 1 | 5 | 16 | 20 | 0 | 0 | |
| 8 | PVA (carbonyl gr. cont. 0.5 mol % or less; pol. deg. 1700) | Ethylene glycol 30% | 0.1 | 1 | 0.1 | 18 | 10 | noisy | X | unstable |
| 9 | PVA (carbonyl gr. cont. 0.5 mol % or less; pol. deg. 1700) | Ethylene glycol 30% | 0.1 | 1 | 1 | 16 | 20 | 0 | 0 | |
| 10 | PVA (carbonyl gr. cont. 0.5 mol % or less; pol. deg. 1700) | Ethylene glycol 30% | 0.1 | 1 | 10 | 15 | 60 | 0 | 0 | |
| 11 | PVA (carbonyl gr. cont. 0.5 mol % or less; pol. deg. 1700) | Ethylene glycol 30% | 0.1 | 1 | 20 | 14 | 120 | 0 | X | too long response time |
| 12 | PVA (carbonyl gr. cont. 0.5 mol % or less; pol. deg. 1700) | Ethylene glycol 30% | 0.1 | $10^{-3}$ | 5 | — | — | noisy | X | unstable |
| 13 | PVA (carbonyl gr. cont. 0.5 mol % or less; pol. deg. 1700) | Ethylene glycol 30% | 0.1 | $10^{-1}$ | 5 | 18 | 20 | 0 | 0 | |
| 14 | PVA (carbonyl gr. cont. 0.5 mol % or less; pol. deg. 1700) | Ethylene glycol 30% | $10^{-3}$ | 1 | 5 | 7 | 20 | 0 | X | insufficient sensitivity |
| 15 | PVA (carbonyl gr. cont. 0.5 mol % or less; pol. deg. 1700) | Ethylene glycol 30% | $10^{-2}$ | 1 | 5 | 18 | 25 | 0 | 0 | |
| 16 | PVA (carbonyl gr. cont. 0.5 mol % or less; pol. deg. 1700) | Ethylene glycol 30% | 1 | 1 | 5 | 14 | 120 | 0 | X | too long response time |

*1 Polyhydroxyethyl methacrylate
*2 Ethylene-vinylalcohol copolymer (ethylene content 33 mol %, moisture content 60 wt % or less)

What is claimed is:

1. A gas sensor comprising:
   a pH-sensitive FET transducer having a gate-insulated field-effect transistor structure;
   a reference electrode deposited on the surface of said transducer and adjacent the gate region of said transducer;
   an insulating tube which provides connecting lead wires to the FET transducer and to the reference electrode and which houses said transducer and reference electrode, said gate region of said FET transducer being located in the opening provided in said insulating tube, and said lead wires extending along said insulating tube;
   electrical insulation resin placed between the inner wall of said tube and lead-wire-FET connecting points to stop said opening of the tube;
   a hydrophilic polymer layer extending over both said gate region of the FET transducer and said reference electrode and containing electrolyte which is sensitive to variations in hydrogen ion concentration through gas absorption; and
   a gas permeable membrane covering at least the entirety of said polymer layer.

2. The gas sensor of claim 1, wherein the surface of said gate region of the pH-sensitive FET transducer is covered with a layer of silicon nitride, alumina, tantalum pentoxide or tantalum nitride.

3. The gas sensor of claim 1, wherein said pH-sensitive FET transducer has an elongated configuration with said gate region located at the front end thereof and an electrode region at the opposite end.

4. The gas sensor of claim 1, wherein the opening provided in the insulating tube is located at the front end of the tube or on the side wall thereof.

5. The gas sensor of claim 1 or 4, wherein said insulating tube is a flexible slender tube capable of being inserted into a living body.

6. The gas sensor of claim 1, wherein said reference electrode comprises a silver layer deposited on the surface of the FET transducer and a silver chloride layer formed thereon.

7. The gas sensor of claim 6, wherein the silver layer has a thickness of at least 3$\mu$ and the silver chloride layer has a thickness of at least 7$\mu$.

8. The gas sensor of claim 6, wherein a bonding layer is provided between the substrate of the FET transducer and the silver layer.

9. The gas sensor of claim 8, wherein said bonding layer is a chromium layer having a thickness of 100–1000 Å.

10. The gas sensor of claim 1, wherein the electrolyte-containing hydrophilic polymer has a moisture content of at least 60% and is selected from the group consisting of polyvinyl alcohol, cellulose, polyhydroxyethyl methacrylate, polyvinyl pyrrolidone, agar-agar, starch and electrolytic polymer.

11. The gas sensor of claim 10, wherein the polyvinyl alcohol is plasticized with a plasticizer.

12. The gas sensor of claim 11, wherein the plasticizer is selected from the group consisting of glycerin, diethylene glycol, ethylene glycol and 3-methyl-1,2,5-trihydroxy pentane.

13. The gas sensor of claim 1 or 10, wherein the hydrophilic polymer is $1-10\mu$ thick in the dry state.

14. The gas sensor of claim 1, wherein the electrolyte is a mixed solution of $NaHCO_3$ and $NaCl$.

15. The gas sensor of claim 1, wherein said gas permeable membrane is a fluoroplastic, a polyolefin plastic or a silicone resin.

16. The gas sensor of claim 15, wherein the gas-permeable membrane is a polytetrafluoroethylene membrane having a thickness of $3-20\mu$.

17. The gas sensor of claim 15, wherein the gas-permeable membrane is a silicon membrane having a thickness of $50-300\mu$.

18. The gas sensor of claim 1, wherein the reference electrode is deposited in less than 2 mm from the gate region of the FET transducer.

* * * * *